(12) United States Patent
Alhanbali

(10) Patent No.: US 10,478,119 B2
(45) Date of Patent: Nov. 19, 2019

(54) SYSTEM AND METHOD FOR DRUG DOSAGE MEDICAMENT REGIME ADHERENCE MONITORING

(71) Applicant: Othman Abdulrahim Radi Alhanbali, Sydney (AU)

(72) Inventor: Othman Abdulrahim Radi Alhanbali, Sydney (AU)

( * ) Notice: Subject to any disclaimer, the term of this patent is extended or adjusted under 35 U.S.C. 154(b) by 355 days.

(21) Appl. No.: 15/486,311

(22) Filed: Apr. 13, 2017

(65) Prior Publication Data
US 2018/0271437 A1 Sep. 27, 2018

(30) Foreign Application Priority Data

Mar. 24, 2017 (AU) .................. 2017201991

(51) Int. Cl.
*A61B 5/00* (2006.01)
*A61J 7/04* (2006.01)
(Continued)

(52) U.S. Cl.
CPC .......... *A61B 5/4833* (2013.01); *A61B 5/7267* (2013.01); *A61J 7/0481* (2013.01);
(Continued)

(58) Field of Classification Search
CPC ...... A61B 5/4833; G16H 20/13; A61J 7/0481
(Continued)

(56) References Cited

U.S. PATENT DOCUMENTS 7,715,277 B2* 5/2010 de la Huerga ........ A61J 7/0084
368/10
7,978,564 B2* 7/2011 De La Huerga .. A61M 5/14212
221/15
(Continued)

*Primary Examiner* — Eric Blount
(74) *Attorney, Agent, or Firm* — Diederiks & Whitelaw, PLC.

(57) ABSTRACT

There is provided a method for oral drug dosage medicament regime adherence monitoring comprising creating an oral drug dosage medicament regime for a patient, the medicament regime having a plurality of medicament intervals for the oral consumption of a plurality of oral drugs, loading the plurality of oral drugs into a cartridge of an oral drug dispensing device, providing a patient wearable vital sign monitoring device for being worn by the patient and associating the patient wearable vital sign monitoring device and the oral drug dispensing device with a patient profile, the patient profile being further associated with the oral drug dosage medicament regime. Then, for at least one medicament interval, the method comprises: alerting the patient of the medicament interval using at least one of the patient wearable vital sign monitoring device and the oral drug dispensing device; obtaining first vital sign measurement data for the patient using the patient wearable vital sign monitoring device; detecting the dispensing of an oral drug from the cartridge of the of oral drug dispensing device; obtaining second vital sign measurement data for the patient post the dispensing using the patient wearable vital sign monitoring device, and comparing the first and second vital sign measurement data to calculate a probability of the oral consumption of the oral drug.

16 Claims, 3 Drawing Sheets

(51) Int. Cl.
    *A61B 5/0205*     (2006.01)
    *A61B 5/145*      (2006.01)
    *A61B 5/1455*     (2006.01)
    *A61B 5/021*      (2006.01)
    *A61B 5/08*       (2006.01)

(52) U.S. Cl.
    CPC ............ *A61B 5/0022* (2013.01); *A61B 5/021* (2013.01); *A61B 5/02055* (2013.01); *A61B 5/0816* (2013.01); *A61B 5/14532* (2013.01); *A61B 5/14551* (2013.01); *A61J 2200/30* (2013.01)

(58) Field of Classification Search
    USPC .................................................. 340/539.12
    See application file for complete search history.

(56) References Cited

U.S. PATENT DOCUMENTS

| | | |
|---|---|---|
| 8,193,918 B1 | 6/2012 | Shavelsky et al. |
| 9,235,683 B2 * | 1/2016 | Robertson ........... G06F 19/3418 |
| 9,870,450 B2 * | 1/2018 | Blackburn ............ A61J 7/0076 |
| 2005/0031536 A1 | 2/2005 | Gryczynski et al. |
| 2007/0135691 A1 | 6/2007 | Zingelewicz et al. |
| 2012/0006700 A1 * | 1/2012 | Geboers ................ A61J 7/0084 206/216 |
| 2012/0157793 A1 | 6/2012 | MacDonald |
| 2012/0165975 A1 | 6/2012 | Yi et al. |
| 2013/0002795 A1 | 1/2013 | Shavelsky et al. |
| 2014/0207278 A1 | 7/2014 | Czaja et al. |
| 2016/0188839 A1 | 6/2016 | Kaul et al. |

* cited by examiner

SYSTEM AND METHOD FOR DRUG DOSAGE MEDICAMENT REGIME ADHERENCE MONITORING

FIELD OF THE INVENTION

The present invention relates to patient self-medicating drug dispensing apparatus and in particular, but not necessarily entirely, to system and method for drug dosage medicament regime adherence monitoring.

The embodiments described herein are described with reference to a preferred embodiment of oral drug dosage medicament regime adherence but the invention may be utilised for other drug dosage regimes such as injections, suppositories, eyedrops and the like.

BACKGROUND OF THE INVENTION

Oral drug dispensing devices are commonplace today in use for dispensing oral drugs in accordance with a dosage regime.

As such, patients can essentially self-medicate under the guidance or supervision of the drug dispensing device.

However, problems exist with such arrangements in that certain patients, such as recalcitrant children, depressed patients or the like, may not consume such dispensed drugs and, for example, only dispense the drug from the dispensing device to satisfy drug dispensing monitoring requirements but not necessarily consume the dispensed drug.

The present invention seeks to provide a system and method for oral drug dosage medicament regime adherence monitoring, which will overcome or substantially ameliorate at least some of the deficiencies of the prior art, or to at least provide an alternative.

It is to be understood that, if any prior art information is referred to herein, such reference does not constitute an admission that the information forms part of the common general knowledge in the art, in Australia or any other country.

SUMMARY OF THE DISCLOSURE

According to one aspect, there is provided a method for oral drug dosage medicament regime adherence monitoring comprising: creating an oral drug dosage medicament regime for a patient, the medicament regime having a plurality of medicament intervals for the oral consumption of a plurality of oral drugs, loading the plurality of oral drugs into a cartridge of an oral drug dispensing device; providing a patient wearable vital sign monitoring device for being worn by the patient, associating the patient wearable vital sign monitoring device and the oral drug dispensing device with a patient profile, the patient profile being further associated with the oral drug dosage medicament regime, wherein, for at least one medicament interval, the method comprises: alerting the patient of the medicament interval using the patient wearable vital sign monitoring device; obtaining first vital sign measurement data for the patient using the patient wearable vital sign monitoring device; detecting the dispensing of an oral drug from the cartridge of the of oral drug dispensing device; obtaining second vital sign measurement data for the patient post the dispensing using the patient wearable vital sign monitoring device, and comparing the first and second vital sign measurement data to calculate a probability of the oral consumption of the oral drug.

The vital sign measurement data may be indicative of at least one of heart rate, blood pressure, respiratory rate, body temperature, blood glucose levels and pulse oximetry measurements.

The vital sign data may represent more than one vital sign measurement.

Coordinating the probability may comprise calculating the probability in accordance with the more than one vital sign measurements.

The probability may be a binary value.

Calculating the probability may comprise utilising a deviation threshold.

The probability may be a scalar vale.

Calculating the probability may comprise utilising a probability distribution.

The method may further comprise ascertaining the proximity of the patient wearable vital sign monitoring device and the oral drug dispensing device substantially at the time of the detecting of the dispensing of the oral drug from the cartridge.

The ascertaining of the proximity may comprise establishing a short-range radio frequency communication channel between the patient wearable vital sign monitoring device and the oral drug dispensing device.

The ascertaining of the proximity may comprise obtaining location data obtained by both of the patient wearable vital sign monitoring device and the oral drug dispensing device and calculating a proximity distance utilising the location data.

The ascertaining of the proximity may comprise obtaining location data obtained by the patient wearable vital sign monitoring device and calculating a proximity distance utilising the location data and a known location of the oral drug dispensing device.

The method may further comprise utilising a supervised machine learning technique to optimise parameters in accordance with historical vital sign response data and calculating the probability in accordance with the parameters.

The parameters may be further optimised in accordance with drug data.

The parameters of further optimised in accordance with patient data.

The parameters may be artificial neural network weightings and wherein calculating the probability further may comprise utilising an artificial neural network configured utilising the artificial neural network weightings.

Other aspects of the invention are also disclosed.

BRIEF DESCRIPTION OF THE DRAWINGS

Notwithstanding any other forms which may fall within the scope of the present invention, preferred embodiments of the disclosure will now be described, by way of example only, with reference to the accompanying drawings in which.

DESCRIPTION OF EMBODIMENTS

Figure 1:
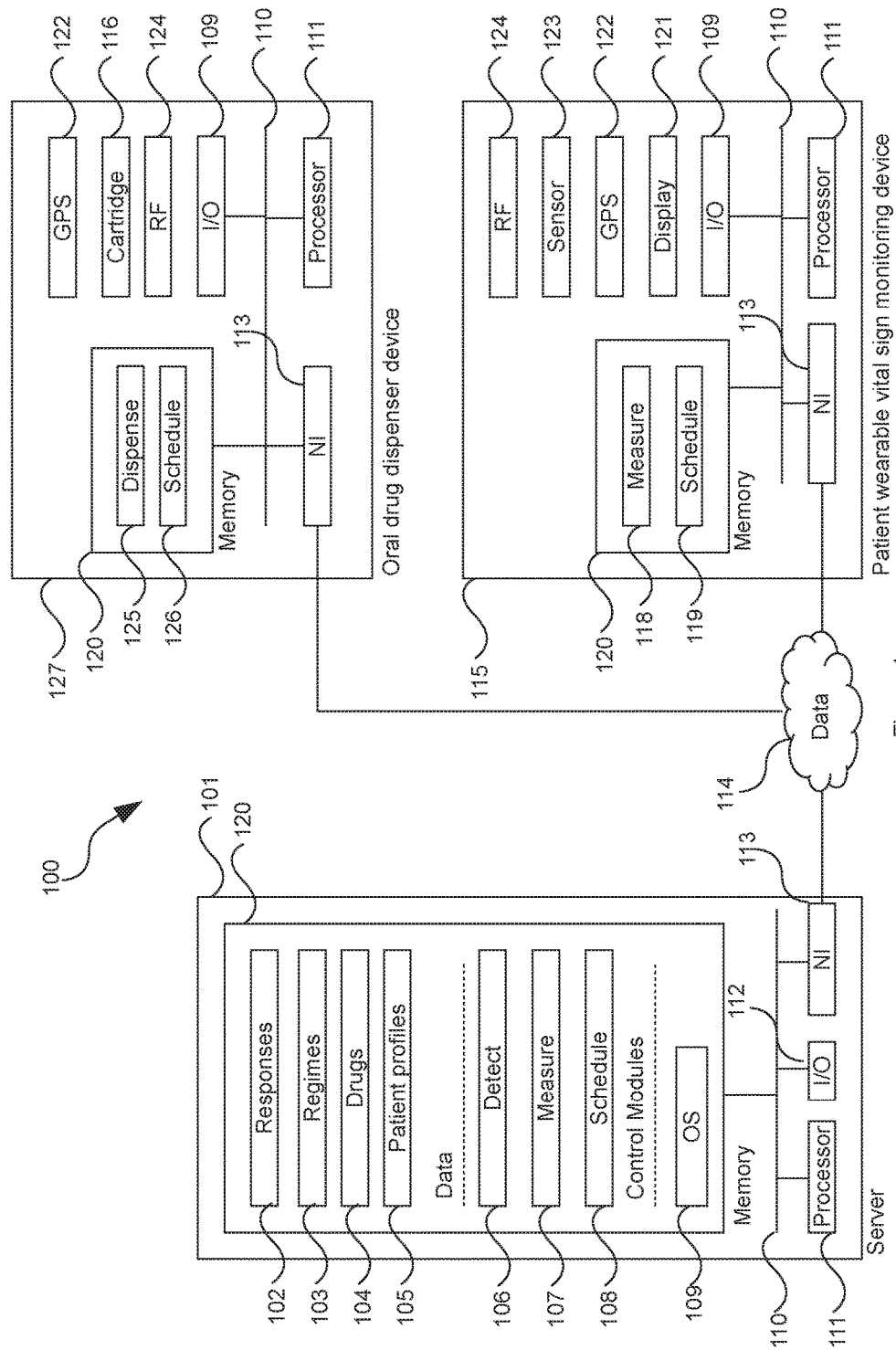
FIG. 1 shows a system for oral drug dosage medicament regime adherence monitoring in accordance with a present embodiment.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure.

Before the structures, systems and associated methods relating to the system and method for oral drug dosage medicament regime adherence monitoring are disclosed and described, it is to be understood that this disclosure is not limited to the particular configurations, process steps, and materials disclosed herein as such may vary somewhat. It is also to be understood that the terminology employed herein is used for the purpose of describing particular embodiments only and is not intended to be limiting since the scope of the disclosure will be limited only by the claims and equivalents thereof.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterised by," and grammatical equivalents thereof are inclusive or open-ended terms that do not exclude additional, unrecited elements or method steps.

It should be noted in the following description that like or the same reference numerals in different embodiments denote the same or similar features.

In the embodiments that follow, there is provided a system and associated methodology for oral drug dosage medicament regime adherence monitoring. As will be described in further detail below, the system and methodology can be used to detect whether patients actually consume prescribed oral drugs.

Turning now to FIG. 1, there is shown a system 1 for oral drug dosage medicament regime adherence monitoring.

In the specific computational architecture shown in FIG. 1, the system 100 comprises a patient wearable vital sign monitoring device 115. Furthermore, the system 100 comprises an oral drug dispenser device 127. Yet further, the system 100 may comprise a server 110.

The dispenser device 127, vital sign monitoring device 115 and the server 101 may be in operable communication across a computer data network 114, such as the Internet.

As such, in general terms, the server 101 may be utilised for maintaining patient profiles including oral drug dosage medicament regimes such that, in use, the oral drug dispenser device 127 and the vital sign monitoring device 150 may also be associated with the patient profile for the purposes of monitoring consumption of the prescribed oral drugs.

Further specifically, each of the server 101, vital sign monitoring device 115 and the dispenser device 127 may comprise a processor 111 for processing digital data.

In operable communication with the processor 111 across a system bus 110 is a memory device 120 for storing digital data including computer program code. As such, in use, the processor 101 fetches computer code instructions from the memory device 120 for execution and wherein data results may be stored back in the memory device 120.

As such, the processor 111 may be controlled to operate in accordance with various computer code modules including those shown in FIG. 1 for the specific tasks of oral drug dosage medicament regime adherence monitoring in the manner described herein.

Specifically, and referring specifically to the server 101, there can be seen the memory device 120 comprising various software modules including an operating system 109, various control modules and various data. As such, the operating system 109 may be fetched for execution by the processor 111 during the bootstrap phase. Thereafter, the control modules may act in unison with the data stored within the data modules/databases for the purposes of implementing the computational functionality described herein.

Specifically, and as will be described in further detail below with reference to an exemplary embodiment, the memory device 120 of the server 101 may comprise a scheduling module 108 for scheduling timing intervals of oral drug dosage medicament regimes for patients.

The server 101 may further comprise a measurement module 107 for measuring various patent vital signs in the manner described herein and also for detecting the dispensing of oral drugs from the dispenser device 127. Furthermore, the server 101 may comprise an oral consumption detection module 106 configured to determine the probability of the consumption of an oral drug in accordance with the measurements obtained by the measurement module 107.

For the data, the server 101 may comprise a data, such as a relational database or the like which may comprise various patient profiles 105. The patient profiles may be stored in relation to various oral drugs 104 which are to be taken in accordance with an oral drug dosage medicament regime 103. Furthermore, patient vital sign responses 102 may also be stored within the database.

Furthermore, the patient wearable vital sign monitoring device 115 similarly comprise various software modules for configuring the functionality of the monitoring device 115. As can be seen, the software modules may again comprise a scheduling module 119 for the purposes of managing the oral drug dosage medicament regime including the various timing intervals thereof including in being able to alert the wearer of a treatment regime interval. The monitoring device 150 may further comprise a measurement module for monitoring vital sign measurement data obtained from a vital sign sensor 123.

As can also be seen, the monitoring device 115 may comprise an I/O module 109 for interfacing with various computer peripherals including a digital display device 121 for the purposes of displaying digital data to the user, including regime treatment interval data. Furthermore, the device 150 may comprise a GPS receiver 122 for ascertaining the location of the monitoring device 115 which, in embodiments, and as will be described in further detail below, may be utilised for the purposes of detecting the proximity of the monitoring device 115 to the dispensing device 127.

As alluded to above, the monitoring device 150 may comprise a vital sign sensor 123 which, may be configured for monitoring various vital signs of the user such as heart rate, blood pressure, respiratory rate, body temperature, blood glucose levels, pulse oximetry and other vital signs. As will be described in further detail below, the system 100 is configured for monitoring these vital signs for detecting the probability of the consumption of an oral drug.

Furthermore, the monitoring device 150 may comprise a short-range radiofrequency transceiver 124 (such as a Bluetooth transceiver) which, in embodiments as will be described in further detail below may further be utilised for the purposes of detecting the proximity of the monitoring device 115 to the dispenser device 127.

Considering now the dispenser device 127, as can be seen, the dispenser device 127 may further comprise software modules. In embodiments, the dispenser device 127 may take the form of a low powered firmware based (such as an FPGA device) computer device.

The software modules of the dispenser device 127 may similarly comprise a schedule module 126 for controlling the scheduling of the timing intervals of the oral drug dosage medicament regime and, furthermore, a dispensing model 125 for controlling the dispensing of one or more of the oral drugs.

As regard, as can be seen, the dispenser device 127 may further comprise an I/O interface 109 which may interface with a drug dispenser cartridge 116. As will be described in further detail below, the drug dispenser cartridge 116 may be loaded with various oral drugs such that, in use, the dispenser device 127 is able to dispense drugs from the cartridge 116 at the appropriate timing intervals.

Furthermore, the dispenser device 127 may further comprise a GPS 122 and a short range radiofrequency transceiver 124 which, similarly, and as will be described in further detail below, may be utilised for the purposes of detecting the proximity of the dispenser device 127 and the vital sign monitoring device 115.

As alluded to above, the server 101, monitoring device 115 and dispenser device 127 may be in operable communication across the data network 114.

As such, both the monitoring device 115 and the dispenser device 127 may receive the oral drug dosage medicament regime data from the server 101 and furthermore, send data back to the server 101 for monitoring purposes wherein, for example, the monitoring device 115 may send back vital sign measurement data to the server 101 and the dispenser device 127 may send back drug dispensing data to the server 101. As such, the server 101 is able to use the vital sign measurement data and drug dispensing data for the purposes of correlating the probability of oral drug consumption.

It should be noted that the architecture provided in FIG. 1 is exemplary only and that modifications may be made thereto within the purposive scope of the embodiments provided herein. For example, the oral drug dispenser device 127 need not necessarily comprise processing capabilities in the manner described above in lieu of taking the form more of a mere drug container wherein access to the drugs are monitored rather with the vital sign monitoring device 115. For example, the dispenser device 127 may take the form of a pillbox or the like wherein the monitoring device 115 is able to record data (such as by capturing image data, reading appropriately located RFID tags and the like) so as to be able to detect retrieval of oral drugs from the pillbox.

Furthermore, the system 100 need not necessarily comprise the server architecture in the manner shown in FIG. 1 in lieu of the vital sign monitoring device 115 performing certain or all of the computational functionality currently shown as being performed by the server 101 in FIG. 1.

As such, as can be appreciated, various modifications may be made to the system architecture of FIG. 1 wherein however, the immutable feature of present embodiments however is that vital sign measurement data is used to detect the probability of oral consumption of a drug.

Method for Oral Drug Dosage Medicament Regime Adherence Monitoring

Figure 2:
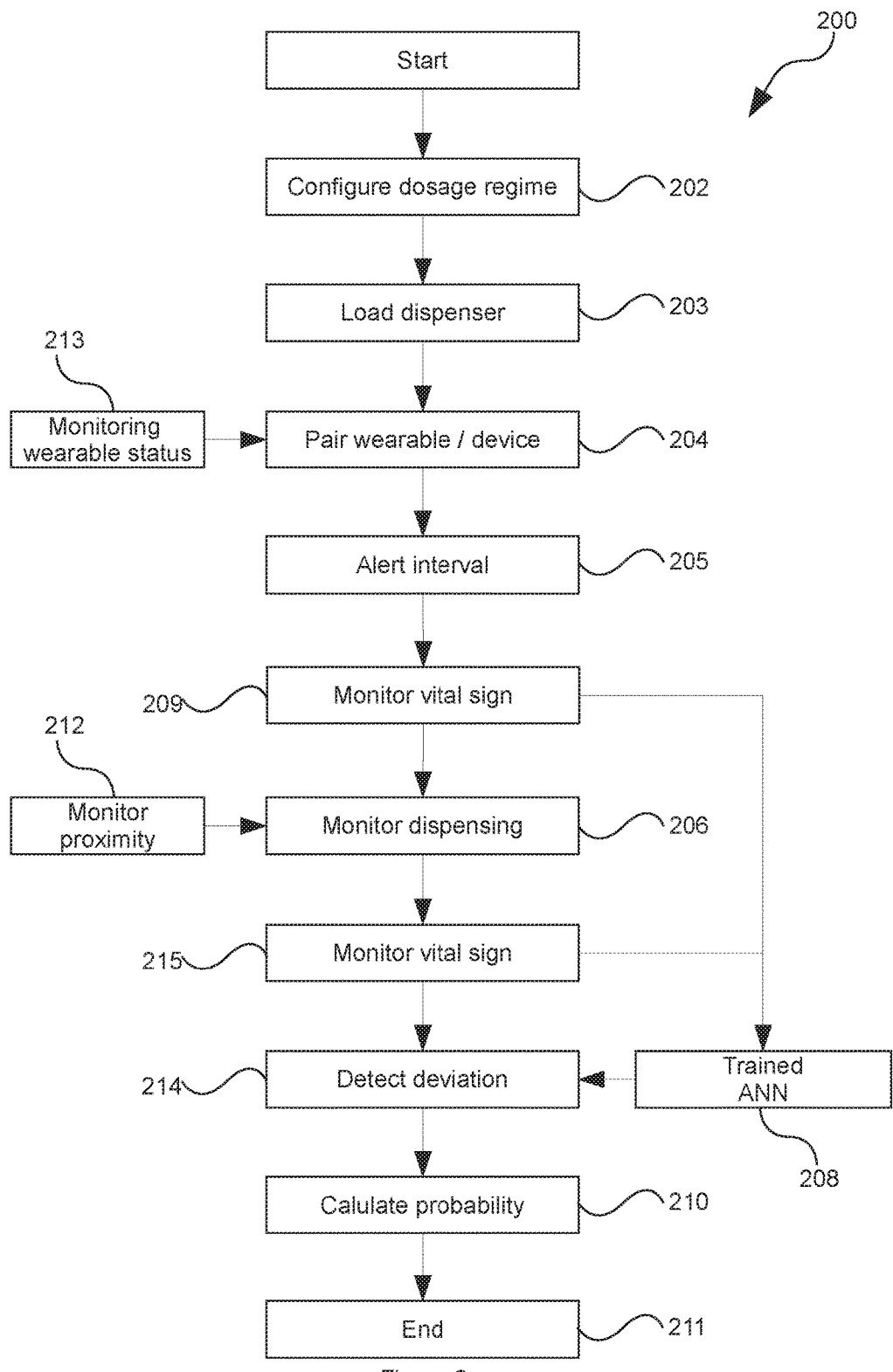
FIG. 2 shows a method for oral drug dosage medicament regime adherence monitoring in accordance with a present embodiment.

Having described the above computational architecture, there will now be described a method 200 for oral drug dosage medicament regime adherence monitoring as a substantially shown in FIG. 2.

Again, should be appreciated that the methodology 200 is provided primarily for illustrative purposes and that no technical limitation should necessarily be imputed to all embodiments accordingly.

Now, the method 200 starts at step 202 wherein an oral drug dosage medicament regime is configured for a patient.

Specifically, the treatment regime may be specified by a treatment doctor and written on a prescription slip which is then taken to a pharmacist for provision thereof.

The pharmacist may then load the cartridge 116 of the oral drug dispenser device 127 with the prescribed oral drugs. Specifically, the cartridge 116 may comprise a separate compartment for each day of the week so as to be able to contain the prescribed drugs for one week. In further in embodiments, the cartridge 116 may be configured for containing drugs for longer periods.

The patient may then be provided with the vital sign monitoring device 115. In embodiments, the vital sign monitoring device 115 may take the form of a conventional wearable, fitness tracking device or the like such as an Apple Watch device which has been configured with the appropriate software modules for implementing the various functionality described herein.

At step 204, the monitoring device 115 and the dispenser device 127 are paired with a patient profile 105 within the database of the server 101. For example, the pharmacist, utilising a pharmacist client terminal (not shown) in operable communication with the server 101 may input a serial number of the dispenser device 127 so as to allow the server 101 to associate a particular dispenser device 127 with the patient profile 105 within the database.

Additionally, the monitoring device 115 may authenticate or communicate with the server 101 for reporting patient ID or other identification data (such as name, contact information and the like) such that the server 101 is able to associate the monitoring device 115 and the dispenser device 127 with a particular patient profile.

The patient profile is associated with the oral drug dosage medicament regime 103 so as to allow the system 100 to control the dispenser device 127 and monitoring device 115 accordingly.

The oral drug dosage medicament regime 103 may be sent across a data network 115 to the wearable device 115 and dispenser device 127 so as to allow these devices to act accordingly, including in the manner described herein.

In embodiments, the method 200 comprises monitoring the wearable status 213 of the wearable 115. The monitoring of the wearable status 230 may be utilised, for example, for detecting whether the patient has removed the wearable device 115.

Monitoring the wearable status 230 may comprise continually monitoring the vital signs of the patient utilising the vital signs sensor 123, such as by continually monitoring the patient's heart rate, body temperature or the like.

As such, should the wearable device 115 fail to detect such vital signs, an alert may be generated for the rectification of the situation.

In embodiments, the monitoring of the wearable status may be confined to particular periods of the day so as to allow the patient to remove the monitoring device 115 at night, when bathing or the like.

Generally, the monitoring of the wearable status 213 need only be conducted around times of treatment intervals so as to ensure that the wearable device 115 is worn when the patient is supposed to take an oral drug so as to allow for the monitoring of the consumption of the oral drug.

Now, at step 205, the wearable device 115 may alert the patient as to a treatment interval. For example, the wearable device 115 may vibrate, display information on the display device or the like informing the patient that the patient is to take a particular oral drug or drugs at a particular time.

Then, at step 209, the wearable device 115 is configured for monitoring and recording vital sign measurement data of the patient. As alluded to above, and as will be described in further detail below, the vital sign measurement data obtained from the patient as compared before and after the dispensing of the oral drug so as to be able to detect a biometric response to the taking of the drug so as to be able to detect the probability of the consumption of the oral drug.

As such, having issued the alert to the patient, the monitoring device 115 begins monitoring the vital signs of the patient. As alluded to above, the monitoring device 115, utilising the sensor 123 may monitor various vital signs including those listed above.

The monitoring device 115 may send the measured vital sign measurement data to the server 101. In embodiments, the monitoring device 115 may send raw measurement data or alternatively derivations thereof such as, for example, average heart rate or the like.

Then, at step 206, the dispenser device 127 is configured for detecting the dispensing of an oral drug. For example, the cartridge 116 may allow selective access to the appropriate compartment for the particular treatment interval and may further indicate the appropriate compartment with an appropriate display for the patient, such as an illuminated indicator adjacent the appropriate compartment.

In embodiments, the dispenser device 127 may be configured for detecting the opening of the cartridge 116 so as to be able to play out audio instructions. Specifically, the memory device 120 may comprise audio files, or text and text-to-speech capabilities configured to play out instructions for the consumption of the drug or other audio messages.

In embodiments, the system 100 at step 212 may be configured for monitoring the proximity of the patient to the dispenser device 127 so as to be able to detect unauthorised dispensing of the oral drugs such as wherein, for example, the drugs may be dispensed to another person.

As alluded to above, in one embodiment, both the monitoring device 115 and the dispenser device 127 may determine their respective locations utilising the GPS receiver 122. As such, the proximity of the patient to the dispenser device 127 may be collected in accordance with the respective GPS locations received via the GPS receivers 122. In alternative embodiments, in lieu of the dispenser device 127 comprises a GPS receiver 122, the known location of the dispenser device 127 (such as a Street address or the like) may be utilised rather.

In alternative embodiments, as opposed to utilising GPS receivers 122, the monitoring device 115 may communicate with the dispenser device 127 using the short range radiofrequency transceiver 124. For example, utilising Bluetooth, the monitoring device 150 may pair with the dispenser device 127 such that there proximity is ascertained by the successful pairing of the Bluetooth transceiver.

It should be noted that, in embodiments, as opposed to the dispenser device 127 communicating with the server 101 across the data network 114, the dispenser device 127 may rather communicate via the short range radiofrequency transceiver is 124 with the monitoring device 115.

For example, the opening of a compartment of the cartridge 160 may be communicated by the dispenser device one and 27 to the monitoring device 115 utilising the Bluetooth interface wherein the opening of the appropriate compartment may be then communicated via the monitoring device 115 to the server 101.

At step 215, having detected the dispensing of the oral drug at step 206, the system 100 is configured for obtaining further vital sign measurement data.

As such, at step 214, the system 100 is able to detect deviations between the vital sign measurement data obtained before the dispensing of the oral drug and after so as to be able to calculate the probability of the oral consumption of the oral drug at step 210.

For example, the consumption of an oral drug may have the effect of lowering (or even raising) the blood pressure, heart rate, blood glucose levels or other vital signs including combinations thereof. As such, the known, previously measured or expected deviations in the vital signs may be utilised for detecting the probability of the taking of the oral consumption.

For example, should the vital signs indicate no statistically significant deviation, the system 100 may calculate a low probability of the consumption of the oral drug so as to be able to take appropriate action, such as by sending an alert notification to the treatment doctor or the like.

In embodiments, the vital sign deviation essentially be hardcoded and the server 101 configurations settings and the probability output represent a binary output wherein, for example, should the patients' blood pressure not to drop by a certain threshold amount within a certain time period, it is determined by the server 100 and one that the patient has not taken the oral drug.

In further embodiments, probability distribution curves may be utilised wherein, for example, a probability may be correlated by the server 101 so as to be able to inform the treatment doctor, for example, that there is only a 20% chance that the patient is in fact taken the oral drug.

As alluded to above, the probability compilation may be multifactorial wherein a combination of vital signs are utilised for determining the probability.

Now, in embodiments, step 208, supervised machine learning, such as which may be used for optimising a trained artificial neural network may be utilised for detecting the probability of the oral consumption of the medicament. The trained artificial neural network 208 may have as input an output the probability of the consumption of the oral drug the vital sign measurement data received pre and post the dispensing of the oral drug.

Figure 3:
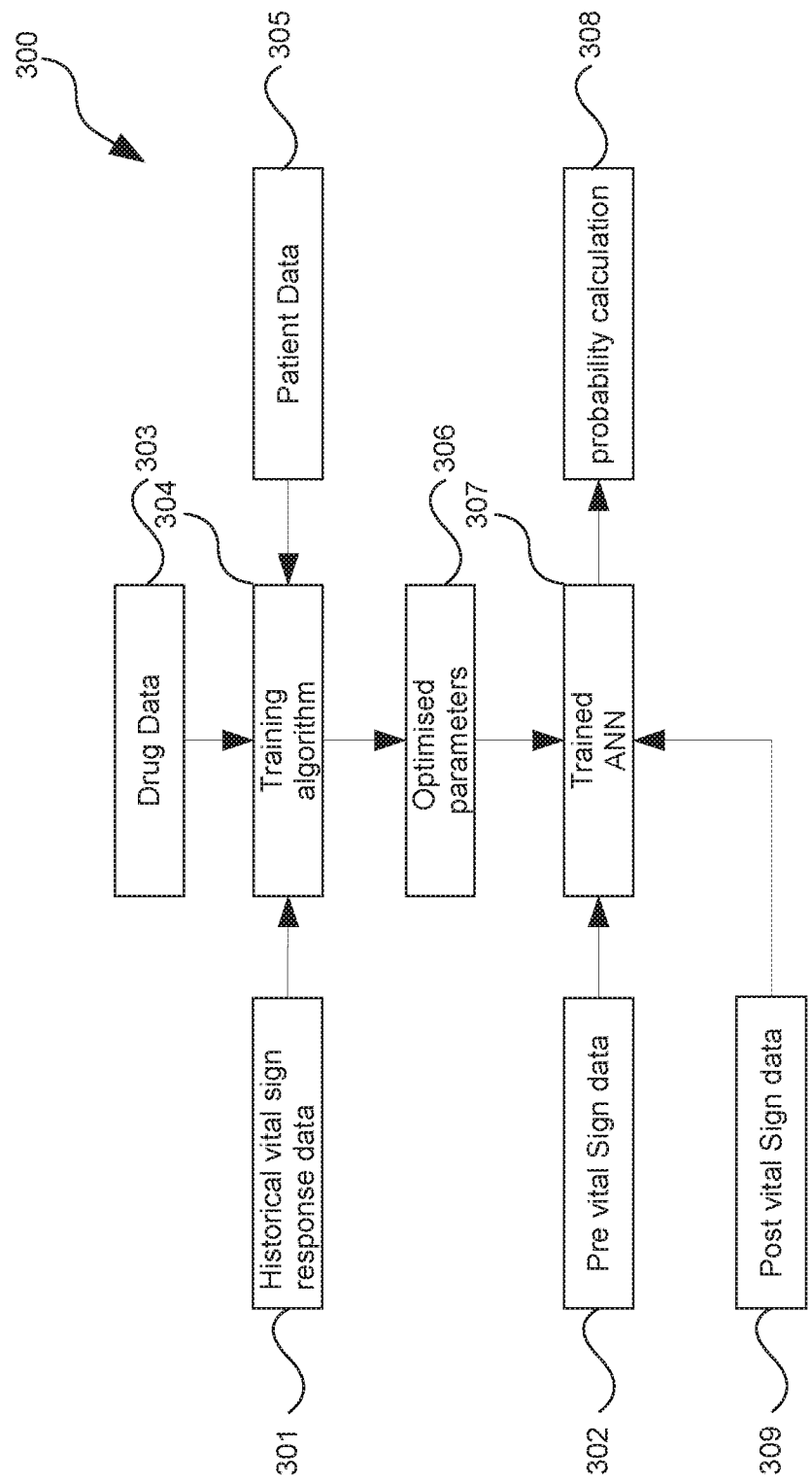
FIG. 3 shows a supervised machine learning optimised artificial neural network for calculating oral consumption probabilities in accordance with pre- and post input vital sign measurement data.

Specifically, turning to FIG. 3, there is shown an exemplary supervised machine learning architecture 300.

As can be seen, for the specific implementation shown, the architecture 300 may comprise a trained artificial neural network 307 which is optimised using optimised parameters 306. The optimised parameters 306 may be obtained utilising a machine learning training algorithm 304 which trains on historical vital sign response data 301 and potentially other data also, including drug data 303 and patient data 305.

The patient data may represent various patient data such as demographic data, such as gender, age, medical history and the like. The drug data 303 may represent a specific drug, drug category, drug dosage amount and the like. The historical vital sign response data 301 may represent historical data for the one or more vital signs alluded to above.

As such, the training algorithm 304 is able to identify co-variances between the various available data so as to be able to allow the artificial neural network 307 to perform the probability calculation 308 in a more accurate manner including one which may not be readily be apparent to treatment professionals.

Specifically, having been configured with the optimised parameters 306, the trained artificial neural network 307 may have as input the pre and post vital sign measurement data 302, 309 so as to be able to output a probability calculation 308 of the oral consumption of an oral drug.

As can be appreciated from the foregoing, certain embodiments make it possible to determine whether a patient has taken a medication as prescribed by monitoring changes and vital signs and the like such as blood pressure, heart rate, blood sugar levels, cholesterol levels, body temperature and more.

Additionally, certain embodiments help reduce the risk of overdose especially for elderly people and that the system controls the dispensing of oral medicaments from the cartridge.

Additionally, by utilising the system according to certain embodiments to control the dispensing of medicaments in accordance with a particular regime, adverse effects from drug to drug interaction may be reduced.

Additionally, certain embodiments allow healthcare professionals to monitor several patients simultaneously.

Additionally, certain embodiments allow healthcare professionals to change or modify prescriptions dynamically, such as by notifying the pharmacist such that the oral drug dispenser device 127 adjust to the new treatment regime such that the patient need not even revisit the pharmacist or doctor.

Yet further, certain embodiments are able to detect the removal of the patient wearable vital sign monitoring device 115 which is a risk for children, depressed and/or mentally ill patients and, in yet further certain embodiments, facilitate in locating the patient.

Interpretation

Wireless:

The invention may be embodied using devices conforming to other network standards and for other applications, including, for example other WLAN standards and other wireless standards. Applications that can be accommodated include IEEE 802.11 wireless LANs and links, and wireless Ethernet.

In the context of this document, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some embodiments they might not. In the context of this document, the term "wired" and its derivatives may be used to describe circuits, devices, systems, methods, techniques, communications channels, etc., that may communicate data through the use of modulated electromagnetic radiation through a solid medium. The term does not imply that the associated devices are coupled by electrically conductive wires.

Processes:

Unless specifically stated otherwise, as apparent from the following discussions, it is appreciated that throughout the specification discussions utilizing terms such as "processing", "computing", "calculating", "determining", "analysing" or the like, refer to the action and/or processes of a computer or computing system, or similar electronic computing device, that manipulate and/or transform data represented as physical, such as electronic, quantities into other data similarly represented as physical quantities.

Processor:

In a similar manner, the term "processor" may refer to any device or portion of a device that processes electronic data, e.g., from registers and/or memory to transform that electronic data into other electronic data that, e.g., may be stored in registers and/or memory. A "computer" or a "computing device" or a "computing machine" or a "computing platform" may include one or more processors.

The methodologies described herein are, in one embodiment, performable by one or more processors that accept computer-readable (also called machine-readable) code containing a set of instructions that when executed by one or more of the processors carry out at least one of the methods described herein. Any processor capable of executing a set of instructions (sequential or otherwise) that specify actions to be taken are included. Thus, one example is a typical processing system that includes one or more processors. The processing system further may include a memory subsystem including main RAM and/or a static RAM, and/or ROM.

Computer-Readable Medium:

Furthermore, a computer-readable carrier medium may form, or be included in a computer program product. A computer program product can be stored on a computer usable carrier medium, the computer program product comprising a computer readable program means for causing a processor to perform a method as described herein.

Networked or Multiple Processors:

In alternative embodiments, the one or more processors operate as a standalone device or may be connected, e.g., networked to other processor(s), in a networked deployment, the one or more processors may operate in the capacity of a server or a client machine in server-client network environment, or as a peer machine in a peer-to-peer or distributed network environment. The one or more processors may form a web appliance, a network router, switch or bridge, or any machine capable of executing a set of instructions (sequential or otherwise) that specify actions to be taken by that machine.

Note that while some diagram(s) only show(s) a single processor and a single memory that carries the computer-readable code, those in the art will understand that many of the components described above are included, but not explicitly shown or described in order not to obscure the inventive aspect. For example, while only a single machine is illustrated, the term "machine" shall also be taken to include any collection of machines that individually or jointly execute a set (or multiple sets) of instructions to perform any one or more of the methodologies discussed herein.

Additional Embodiments:

Thus, one embodiment of each of the methods described herein is in the form of a computer-readable carrier medium carrying a set of instructions, e.g., a computer program that are for execution on one or more processors. Thus, as will be appreciated by those skilled in the art, embodiments of the present invention may be embodied as a method, an apparatus such as a special purpose apparatus, an apparatus such as a data processing system, or a computer-readable carrier medium. The computer-readable carrier medium carries computer readable code including a set of instructions that when executed on one or more processors cause a processor or processors to implement a method. Accordingly, aspects of the present invention may take the form of a method, an entirely hardware embodiment, an entirely software embodiment or an embodiment combining software and hardware aspects. Furthermore, the present invention may take the form of carrier medium (e.g., a computer program product on a computer-readable storage medium) carrying computer-readable program code embodied in the medium.

Carrier Medium:

The software may further be transmitted or received over a network via a network interface device. While the carrier medium is shown in an example embodiment to be a single medium, the term "carrier medium" should be taken to include a single medium or multiple media (e.g., a centralized or distributed database, and/or associated caches and servers) that store the one or more sets of instructions. The term "carrier medium" shall also be taken to include any medium that is capable of storing, encoding or carrying a set of instructions for execution by one or more of the processors and that cause the one or more processors to perform any one or more of the methodologies of the present invention. A carrier medium may take many forms, including but not limited to, non-volatile media, volatile media, and transmission media.

Implementation:

It will be understood that the steps of methods discussed are performed in one embodiment by an appropriate processor (or processors) of a processing (i.e., computer) system executing instructions (computer-readable code) stored in storage. It will also be understood that the invention is not limited to any particular implementation or programming technique and that the invention may be implemented using any appropriate techniques for implementing the functionality described herein. The invention is not limited to any particular programming language or operating system.

Means for Carrying Out a Method or Function

Furthermore, some of the embodiments are described herein as a method or combination of elements of a method that can be implemented by a processor of a processor device, computer system, or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

Connected

Similarly, it is to be noticed that the term connected, when used in the claims, should not be interpreted as being limitative to direct connections only. Thus, the scope of the expression a device A connected to a device B should not be limited to devices or systems wherein an output of device A is directly connected to an input of device B. It means that there exists a path between an output of A and an input of B which may be a path including other devices or means. "Connected" may mean that two or more elements are either in direct physical or electrical contact, or that two or more elements are not in direct contact with each other but yet still co-operate or interact with each other.

Embodiments:

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the above description of example embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description of Specific Embodiments are hereby expressly incorporated into this Detailed Description of Specific Embodiments, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Different Instances of Objects

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

Specific Details

In the description provided herein, numerous specific details are set forth. However, it is understood that embodiments of the invention may be practiced without these specific details. In other instances, well-known methods, structures and techniques have not been shown in detail in order not to obscure an understanding of this description.

Terminology

In describing the preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar technical purpose. Terms such as "forward", "rearward", "radially", "peripherally", "upwardly", "downwardly", and the like are used as words of convenience to provide reference points and are not to be construed as limiting terms.

Comprising and Including

In the claims which follow and in the preceding description of the invention, except where the context requires otherwise due to express language or necessary implication, the word "comprise" or variations such as "comprises" or "comprising" are used in an inclusive sense, i.e. to specify the presence of the stated features but not to preclude the presence or addition of further features in various embodiments of the invention.

Any one of the terms: including or which includes or that includes as used herein is also an open term that also means including at least the elements/features that follow the term, but not excluding others. Thus, including is synonymous with and means comprising.

Scope of Invention

Thus, while there has been described what are believed to be the preferred embodiments of the invention, those skilled in the art will recognize that other and further modifications may be made thereto without departing from the spirit of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

Although the invention has been described with reference to specific examples, it will be appreciated by those skilled in the art that the invention may be embodied in many other forms.

INDUSTRIAL APPLICABILITY

It is apparent from the above, that the arrangements described are applicable to the medicament dosage machine industries.

The invention claimed is:

1. A method for oral drug dosage medicament regime adherence monitoring comprising:
   creating an oral drug dosage medicament regime for a patient, the medicament regime having a plurality of medicament intervals for the oral consumption of a plurality of oral drugs,
   loading the plurality of oral drugs into a cartridge of an oral drug dispensing device;
   providing a patient wearable vital sign monitoring device for being worn by the patient,
   associating the patient wearable vital sign monitoring device and the oral drug dispensing device with a patient profile, the patient profile being further associated with the oral drug dosage medicament regime, wherein, for at least one medicament interval, the method comprises:
   alerting the patient of the medicament interval using at least one of the patient wearable vital sign monitoring device and the oral drug dispensing device;
   obtaining first vital sign measurement data for the patient using the patient wearable vital sign monitoring device;
   detecting the dispensing of an oral drug from the cartridge of the of oral drug dispensing device;
   ascertaining the proximity of the patient wearable vital sign monitoring device and the oral drug dispensing device at substantially the same time as the detecting of the dispensing of the oral drug from the cartridge;
   obtaining second vital sign measurement data for the patient post the dispensing using the patient wearable vital sign monitoring device, and
   comparing the first and second vital sign measurement data to calculate a probability of the oral consumption of the oral drug.

2. A method as claimed in claim 1, wherein vital sign measurement data is indicative of at least one of heart rate, blood pressure, respiratory rate, body temperature, blood glucose levels and pulse oximetry measurements.

3. A method as claimed in claim 2, wherein the vital sign data represents more than one vital sign measurement.

4. A method as claimed in claim 3, wherein coordinating the probability comprises calculating the probability in accordance with the more than one vital sign measurements.

5. A method as claimed in claim 1, wherein the probability is a binary value.

6. A method as claimed in claim 5, wherein calculating the probability comprises utilising a deviation threshold.

7. A method as claimed in claim 1, wherein the probability is a scalar value.

8. A method as claimed in claim 7, wherein calculating the probability comprises utilising a probability distribution.

9. A method as claimed in claim 1, wherein the ascertaining of the proximity comprises establishing a short-range radio frequency communication channel between the patient wearable vital sign monitoring device and the oral drug dispensing device.

10. A method as claimed in claim 1, wherein the ascertaining of the proximity comprises obtaining location data obtained by both of the patient wearable vital sign monitoring device and the oral drug dispensing device and calculating a proximity distance utilising the location data.

11. A method as claimed in claim 1, wherein the ascertaining of the proximity comprises obtaining location data obtained by the patient wearable vital sign monitoring device and calculating a proximity distance utilising the location data and a known location of the oral drug dispensing device.

12. A method as claimed in claim 1, further comprising utilising a supervised machine learning technique to optimise parameters in accordance with historical vital sign response data and calculating the probability in accordance with the parameters.

13. A method as claimed in claim 12, wherein the parameters are further optimised in accordance with drug data.

14. A method as claimed in claim 12, wherein the parameters are further optimised in accordance with patient data.

15. A method as claimed in claim 12, wherein the parameters are artificial neural network weightings and wherein calculating the probability further comprises utilising an artificial neural network configured utilising the artificial neural network weightings.

16. A method for oral drug dosage medicament regime adherence monitoring comprising:
   creating an oral drug dosage medicament regime for a patient, the medicament regime having a plurality of medicament intervals for the oral consumption of a plurality of oral drugs;
   loading the plurality of oral drugs into a cartridge of an oral drug dispensing device;
   providing a patient wearable vital sign monitoring device for being worn by the patient;
   associating the patient wearable vital sign monitoring device and the oral drug dispensing device with a patient profile, the patient profile being further associated with the oral drug dosage medicament regime, wherein, for at least one medicament interval, the method comprises:
   alerting the patient of the medicament interval using at least one of the patient wearable vital sign monitoring device and the oral drug dispensing device;
   obtaining first vital sign measurement data for the patient using the patient wearable vital sign monitoring device;
   detecting the dispensing of an oral drug from the cartridge of the of oral drug dispensing device;
   obtaining second vital sign measurement data for the patient post the dispensing using the patient wearable vital sign monitoring device;

comparing the first and second vital sign measurement data to calculate a probability of the oral consumption of the oral drug; and utilising a supervised machine learning technique to optimise parameters in accordance with historical vital sign response data and calculating the probability in accordance with the parameters.

\* \* \* \* \*